US00RE38091E

(19) United States
(12) Reissued Patent
Strecker

(10) Patent Number: US RE38,091 E
(45) Date of Reissued Patent: Apr. 22, 2003

(54) DEVICE WITH A PROSTHESIS IMPLANTABLE IN THE BODY OF A PATIENT

(75) Inventor: Ernst Peter Strecker, Karlsruhe (DE)

(73) Assignee: Boston Scientific Corporation, Natick, MA (US)

(21) Appl. No.: 08/834,832

(22) Filed: Apr. 10, 1997

Related U.S. Patent Documents

Reissue of:
(64) Patent No.: 5,405,378
Issued: Apr. 11, 1995
Appl. No.: 07/886,518
Filed: May 20, 1992

(51) Int. Cl.[7] ..... A61F 2/06; A61F 2/04; A61M 29/00

(52) U.S. Cl. ..... 623/1.12; 623/1.11; 623/1.31; 623/1.34; 623/1.38; 623/1.42; 623/1.5; 606/194

(58) Field of Search ..... 623/1, 11, 12, 623/1.1, 1.11, 1.12, 1.23; 606/194, 195

(56) References Cited

U.S. PATENT DOCUMENTS

| | | | |
|---|---|---|---|
| 4,629,459 | A | 12/1986 | Ionescu et al. |
| 4,732,152 | A | 3/1988 | Wallstén et al. |
| 4,878,906 | A | 11/1989 | Lindemann |
| 4,913,141 | A | 4/1990 | Hillstead |
| 4,922,905 | A | 5/1990 | Strecker |
| 5,147,400 | A | 9/1992 | Kaplan et al. |
| 5,234,456 | A | 8/1993 | Silvestrini |
| 5,234,457 | A | 8/1993 | Andersen |
| 5,653,748 | A | 8/1997 | Strecker |

FOREIGN PATENT DOCUMENTS

| | | | |
|---|---|---|---|
| DE | 3640745 | A1 | 6/1987 |
| DE | 35 42 475.3 | * | 6/1987 |
| DE | 4037507 | * | 11/1990 |
| DE | 40 37 507.2 | * | 11/1990 |
| DE | 4137857 | A1 | 5/1992 |
| EP | 0183372 | A1 | 6/1986 |
| EP | 0292587 | B1 | 11/1988 |
| EP | 0382014 | A1 | 8/1990 |
| FR | 2 333 487 | | 7/1977 |
| GB | 1173811 | | 12/1969 |
| GB | 1565828 | | 4/1980 |
| WO | PCT/EP91/02194 | | 6/1992 |

OTHER PUBLICATIONS

Sondheim, Erich; Knoten Spleissen Takeln; 1953; Verlag Klasing & Co. GmbH, Blielefeld, pp. 19–21.

* cited by examiner

*Primary Examiner*—Michael J. Milano
(74) *Attorney, Agent, or Firm*—Finnegan, Henderson, Farabow, Garrett & Dunner, L.L.P.

(57) ABSTRACT

The device comprises a prosthesis designed as a hollow body compressed against the action of restoring spring forces to a cross section reduced relative to an expanded use position, and held in this position by a strippable sheath. After the sheath is stripped, the prosthesis automatically expands to a cross section corresponding to the use position. The sheath, which can be a meshwork in the approximate form of crocheted material, extends over the entire length of the prosthesis and consists of at least one continuous thread and at least one drawstring. The prosthesis, held in the radially compressed position by the sheath, can be mounted displaceably on a feed wire or non-axially-displaceably on the insertion end of a probe or a catheter.

52 Claims, 3 Drawing Sheets

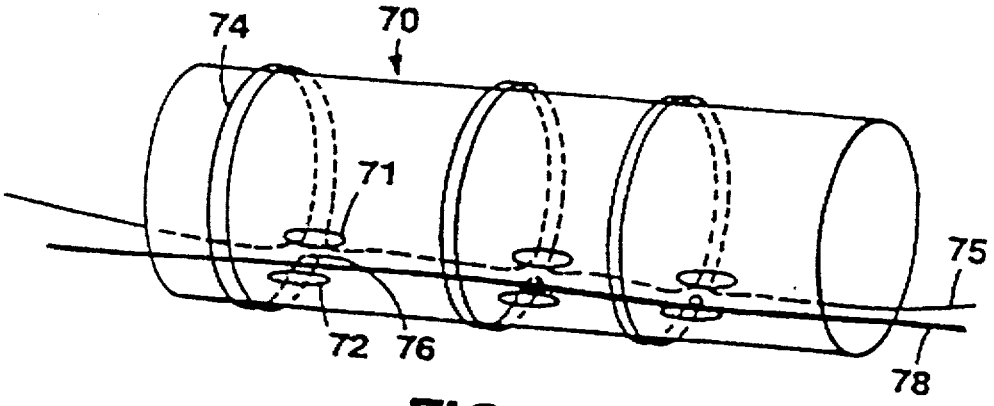
FIG. 7
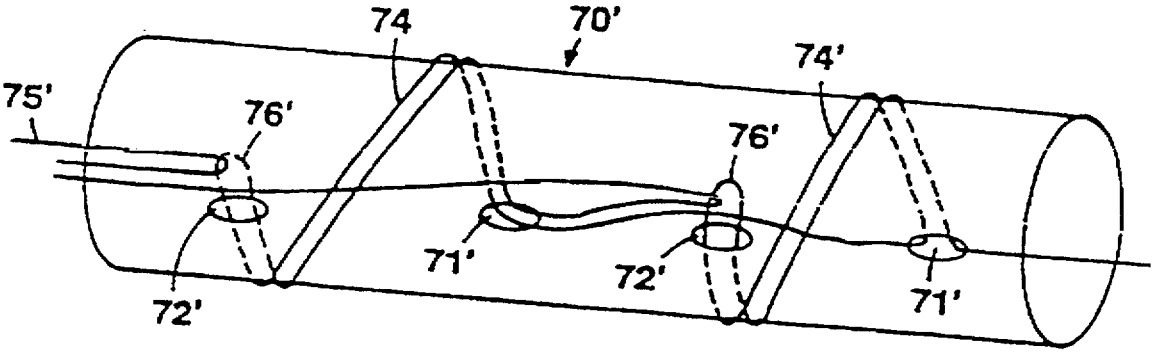
FIG. 8
FIG. 9
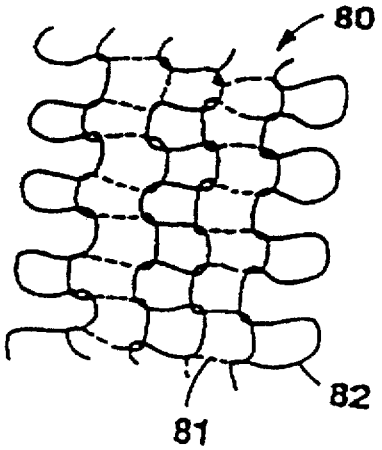

DEVICE WITH A PROSTHESIS IMPLANTABLE IN THE BODY OF A PATIENT

Matter enclosed in heavy brackets [ ] appears in the original patent but forms no part of this reissue specification; matter printed in italics indicates the additions made by reissue.

The invention relates to a device with a prosthesis implantable in the body of a patient, especially in a blood vessel or other body cavity, and designed as a hollow body. The prosthesis is compressible against the action of restoring spring forces down to a cross section which is reduced relative to an (expanded) operating position. The prosthesis may be also automatically expanding to a cross section corresponding to the operating position following removal of the restraining forces effecting the compression.

BACKGROUND

Devices of this type are known, and serve for percutaneous implantation of vascular prostheses in particular. Prostheses which are introducible percutaneously and expand in the lumen are either expandable mechanically by means of a known balloon catheter from a small radius to the larger radius to hold a vascular lumen open, or they expand automatically following previous compression prior to implantation by spring force, due to spring pretensioning generated during compression.

Various systems are already known for inserting self-expanding vascular prostheses which are under spring force into the body of a patient, and to implant or anchor them in the vessel by removing the restraining force.

The commonest method, which is described in EP-A-0 183 372, consists in compressing an endoprosthesis, made in the form of a tubular hollow body, to a reduced cross section and then pushing it in the compressed state, using a so-called pusher, through a catheter previously introduced into a vessel until they are in the correct position in the vessel. However, this system suffers from the disadvantage that a considerable expenditure of force is required to push the prosthesis through the catheter because its displacement is counteracted by considerable frictional forces.

Another method (not confirmable by publications) consists in retracting a sheath covering the endoprosthesis and holding the latter together, in the vessel at the implantation site. Here again there is the disadvantage that high frictional forces must be overcome. Moreover, the tube system is quite rigid because of the sheath covering the prosthesis, making introduction into a vessel through curves very difficult.

In another system (U.S. Pat. No. 4,732,152) a woven and spring-tensioned prosthesis is held together in the compressed state by a double sheath, sealed at the distal end. This sheath is retracted from the folded prosthesis like a stocking being pulled off the foot of a wearer. To reduce the friction which then occurs, liquid can be introduced between the two sheath layers. This system, which initially appears elegant because of the reduction of the frictional resistances, is extremely cumbersome to handle however and requires two persons to operate.

On the other hand, the invention is intended to provide an especially simple and readily operable device for implantation of a prosthesis made in the form of a hollow body, with a vascular prosthesis envisioned in particular.

SUMMARY OF THE INVENTION

This goal is achieved by virtue of the fact that in the device according to the preamble of claim 1 the prosthesis is surrounded by a sheath which can be pulled off it, said sheath consisting of at least one through thread, and compressed to a reduced cross section, and by the fact that at least one drawstring is provided, said drawstring being laid so it extends away from the sheath holding the prosthesis in its radially compressed state, the thread forming said sheath being retractable.

In the invention, the prosthesis is therefore held in its radially compressed state by means of this external sheath and reaches its intended expansion position only after removal of this sheath, which is designed to be pulled off, thanks to the pretensioning force generated during compression.

The sheath can be in particular a meshwork produced by crocheting, knotting, tying, or other methods of mesh formation.

Advantageously the prosthesis, held by the sheath which can be pulled off in the radially compressed state, can be received on a probe, or a flexible guide wire, and advanced thereon. In one design of a device of this kind, implantation is accomplished by introducing the guide wire in known fashion into a vessel and then advancing the prosthesis, held in a radially compressed state, along the guide wire, said wire being advanced for example by means of a sleeve likewise advanced over the guide wire and engaging the end of the prosthesis away from the insertion end thereof.

Another improvement, on the other hand, provides that the prosthesis, held in the radially compressed state by the sheath which can be pulled off, is held in an axially fixed position on the insertion end of a probe. Specifically, this probe can be a catheter advanced over a guide wire.

Even with the axially fixed mounting of the prosthesis, held in the compressed state, on the insertion end of a probe or a catheter, implantation takes place in simple fashion with the probe or catheter being advanced together with the prosthesis mounted on the insertion end, for example under the control of x-rays, up to the implantation site, and then by pulling off the sheath, made for example as a covering meshwork, the prosthesis is exposed and implanted in the proper location by its automatic expansion.

In mounting the prostheses on the insertion ends of probes or catheters, it has been found to be advantageous for the prosthesis to be mounted on a non-slip substrate surrounding the probe or catheter, so that undesired slipping and sliding during the release of the thread material forming the meshwork cannot occur.

Advantageously, the self-expanding prosthesis can be a tube made by crocheting, knitting, or other methods of mesh formation, composed of metal and plastic thread material with good tissue compatibility, said tube being compressible radially against the action of pretensioning forces and automatically expanding into its operating position after the restraining forces are removed, and then remaining in the expanded position.

In the case of the prosthesis designed as meshwork, according to a logical improvement, successive rows of mesh can be made alternately of resorbable thread material and non-resorbable thread material. This means that within a predetermined period of time after implantation, the resorbable thread material will be dissolved and the prosthesis parts, then consisting only of non-resorbable thread material, will remain in the patient's body. These remaining components form circumferential rings of successive open loops. This avoids thread intersections which could exert undesirable shearing forces on surrounding and growing tissue coatings.

In the improvement just described, drugs can also be embedded in the resorbable thread material so that the prosthesis constitutes a drug deposit which gradually dispenses drugs during the gradual dissolution of the resorbable thread material.

An especially advantageous improvement on the invention is characterized by making the tubular meshwork holding the prosthesis in the compressed state in such a way that the mesh changes direction after each wrap around the prosthesis and when successive meshes are pulled off, the thread sections forming the latter separate alternately to the right and left from the prosthesis.

The advantage of this improvement consists in the fact that the mesh wrapped successively and alternately left and right around the prosthesis can be pulled off without the thread material becoming wrapped around the probe holding the prosthesis or a catheter serving as such, or undergoing twisting, which would make further retraction of the thread material more difficult because of the resultant friction.

It has also been found to be advantageous in the improvement described above for the loops or knots of the mesh wrapped successively around the prosthesis and capable of being pulled off, to be located sequentially with respect to one another or in a row running essentially axially.

Another important improvement on the invention provides for the drawstring to extend away from the mesh surrounding the insertion end of the prosthesis, and therefore the prosthesis, as the meshwork is pulled off its distal end, gradually reaches its expanded position.

In this improvement, the thread material to be pulled off when the prosthesis is tightened can never enter the area between the already expanded part of the prosthesis and the wall of a vessel for example. The thread material to be pulled off instead extends only along the part of the mesh which has not yet been pulled off and thus in the area of the prosthesis which is still held in the compressed position.

The ends of the thread material forming the meshwork can be held by releasable knots, in the form of so-called slip knots for example, and thereby have their releasability preserved. One especially simple means that has been found for axial mounting of the prosthesis on a probe or on a catheter serving as such is for the beginning of the thread material forming the meshwork and an end mesh to be pinched in holes in the probe or catheter, yet capable of being pulled out of their pinched positions by means of the drawstring. The beginning of the thread material can be pinched between the probe and the cuff mounted held on the latter, however.

The cuff material is held especially securely, but at the same time in such a way that it can be easily pulled off, if from the knot of the mesh of the first mesh on the pull-off side of the meshwork, a loop passed through a hole extends, one end of said loop making a transition in the vicinity of the above knot to the drawstring. As a result, this loop can be pulled off by means of the drawstring through the above-mentioned knot and then all of the mesh forming the meshwork can be pulled off in succession.

According to another logical improvement on the invention, the prosthesis can also be held in its radially compressed position by means of a meshwork applied from the distal end of the probe or catheter and extending over the insertion end of the prosthesis and by means of a meshwork that extends in the direction opposite the proximal end and also extends over the end mesh of the first meshwork. It has been found advantageous in this connection for the two meshworks to be capable of being pulled off in opposite directions from their loop-shaped end meshes by means of drawstrings.

In a design of this kind, following correct placement of the prosthesis mounted on a probe or a catheter in a vessel, the meshwork applied from the distal end is pulled off first, beginning with the end mesh removed from the distal end and then advancing gradually until this meshwork is removed completely and the thread material is retracted. Then the meshwork applied from the proximal end is pulled off, starting with the end mesh toward the distal end and then advancing toward the proximal end. It is obvious that when the meshwork is pulled off in this way, the self-expanding prosthesis is expanded gradually, starting at its distal end, into its intended operating position.

In another important embodiment, the sheath that holds the prosthesis in its radially compressed position consists of loops surrounding the prosthesis and spaced axially apart, said loops being formed by the thread material, pulled through a hole in the prosthesis, of a thread guided along inside the prosthesis, with the ends of the loops each being brought back through a hole, adjacent to the first hole in the circumferential direction, into the interior of the prosthesis, and a warp thread, likewise running along the inside of the prosthesis and guided through the ends of the loops, holds in the loops in their wrapping positions. It is clear that in this design the prosthesis is released by pulling the warp thread out of the end segments of the loops, and that the thread material forming the loops, like the warp thread, can be retracted in simple fashion. In a similar improvement on the invention, the sheath holding the prosthesis in its radially compressed position consists of loops which are axially spaced apart and are wrapped around the prosthesis, said loops being formed by thread material, pulled through a hole in the prosthesis, of a thread guided along inside the prosthesis, with the ends of the loops each being brought back into the interior of the prosthesis through holes spaced axially from the first hole, and held in place by the fact that a loop formed from the thread material running inside the prosthesis is pulled through each loop end brought back into the prosthesis, said loop then being brought out through a hole following in the axial direction, then being wrapped around the prosthesis and brought back in the same manner with its loop end passing through a hole into the prosthesis and being secured in this position. In this design also, the pulling off of the sheath holding the prosthesis in its radially compressed position is accomplished in simple fashion by means of the thread extending from the last loop, from which the loops surrounding the prosthesis are formed.

For especially tight wrapping and the resultant compression of the prosthesis, it has also been found advantageous to use shrinkable thread material to form the meshwork. The meshwork that can be pulled off can also consist of a plurality of threads running parallel to one another.

Another important improvement on the invention provides that between the prosthesis and the sheath holding the latter in the radially compressed state, at least one additional sheath is provided which loosely fits around the prosthesis and allows a partial expansion of the prosthesis when the outer sheath is pulled off, and is itself subsequently capable of being pulled off.

This improvement is also one that involves a sheath, surrounding the prosthesis loosely and with a certain amount of play, being mounted on said prosthesis, which can be a meshwork, with the prosthesis and the inner sheath being surrounded closely by an outer sheath which holds the prosthesis, together with the sheath mounted directly on it, in the radially compressed state. The prosthesis is consequently surrounded by two layers, so to speak, and after the outer sheath is stripped, can expand only within the limits set by the inner sheath. The final implantation is then accomplished by stripping the inner sheath, i.e. in stages.

Of course, several meshworks surrounding one another with a certain amount of play can be provided, which permit expansion of the prosthesis in several successive stages.

Within the scope of the invention, the spaces between the meshes of a meshwork surrounding the prosthesis and holding it in the compressed state can be filled and smoothed with gelatin or a similar substance which dissolves in the body of a patient. This facilitates introduction of such a device.

According to yet another improvement, at least one end of the prosthesis can be surrounded in the compressed state by a cuff, said end, because of the axial shortening of the prosthesis that takes place during expansion, escaping the grip exerted by the cuff. A cuff of this kind can be mounted permanently on the probe and/or a catheter, with the open side facing the prosthesis, for example on the side toward the distal end. This produces a smooth transition that facilitates introduction, at the end of the prosthesis which is at the front in the insertion device.

For improved attachment of the prosthesis to a probe or to a catheter serving as same, the end of the prosthesis facing away from the insertion end can abut at a radially projecting step or shoulder or a cuff mounted on the probe or catheter.

Yet another improvement on the invention provides that when a catheter is used as a probe, the drawstring is introduced through a hole passing through the catheter wall in the vicinity of one end of the prosthesis, enters the lumen of the catheter, extends through the latter, and extends beyond the end of the catheter.

However, a double-lumen catheter can also serve as a probe with one lumen serving to advance the catheter over a guide wire and the other lumen being used to guide the drawstring.

When using a catheter with one or two lumina as a probe, with the drawstring passing through the catheter lumen, assurance is provided that the walls of the vessels or other body cavities in which a prosthesis is to be implanted cannot be damaged by the drawstring and/or, when the meshwork is stripped, by the thread material, which is then pulled back through the catheter lumen.

It has also proven to be advantageous for the drawstring and/or the thread material of the meshwork to be provided with a friction-reducing lubricant.

In addition, at least the drawstring can be made in the form of a metal thread or provided with an admixture of metal, so that good visibility with x-rays is ensured.

Finally, according to yet another improvement, the prosthesis, kept in the radially compressed position by the strippable sheath, can expand to resemble a trumpet at its proximal end in the expanded state following removal of the sheath,. This prosthesis design is important for implants in the vicinity of branches in the vessels, because there is always the danger of the prosthesis slipping into the branching vessel. In view of the trumpet-shaped expansion at the proximal end, however, such slipping during implantation is effectively suppressed when the sheath surrounding the prosthesis is stripped off the proximal end.

DESCRIPTION

One embodiment of the device according to the invention will now be described with reference to the attached drawing. Schematic views show the following:

FIG. 7 shows the vascular prosthesis alone, held in a radially compressed position by wrapping loops;

FIG. 8 is a view like that in FIG. 7 of a prosthesis in which the loops holding the latter in a radially compressed position are formed by crocheting, and FIG. 9 shows a portion of a vascular prosthesis in the form of knitted fabric.

Figure 1:
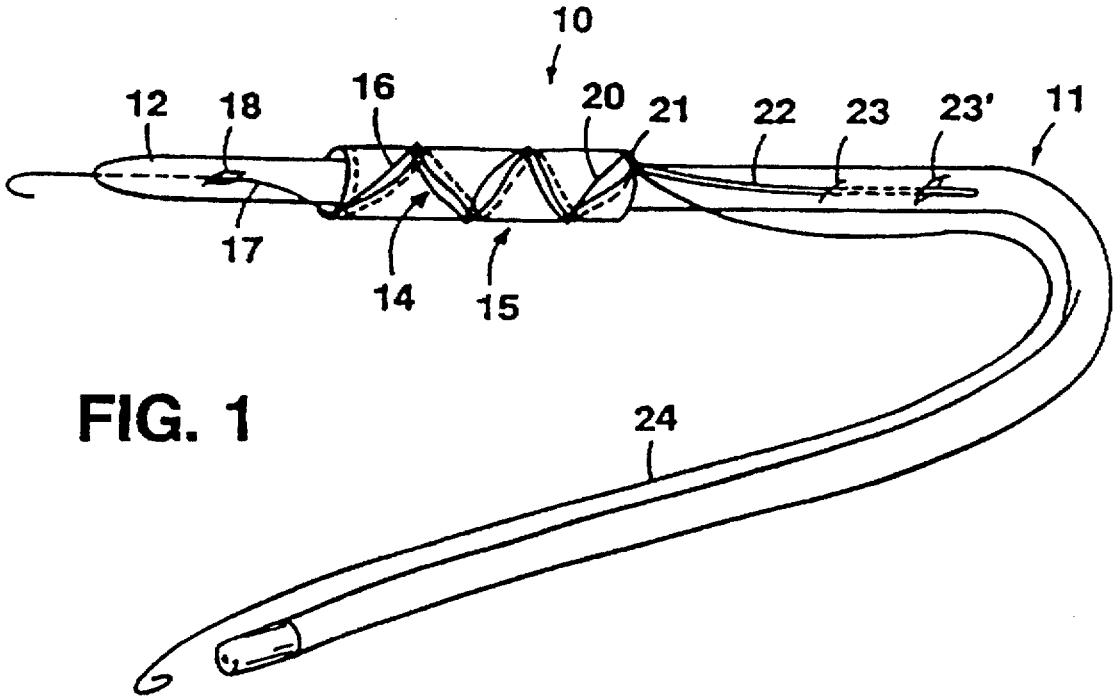
FIG. 1 shows a catheter with a vascular prosthesis mounted on its distal end held under radial pretensioning in the compressed state by a crocheted material in the form of a strippable tubular meshwork.

In device 10 shown in FIG. 1, an elongated catheter 11 serves as a probe, with a through lumen by which the catheter can be advanced in known fashion over a guide wire inserted in a vessel. In the vicinity of its distal end 12, catheter 11 carries a prosthesis 15 held in a compressed position under radial pretensioning by means of a crocheted material 14, said prosthesis, following elimination of the restraining force provided by the crocheted material, changing to its intended expanded position by expanding automatically. For example, the prosthesis can be a tubular knitted fabric radially compressible against the effect of a restoring spring force into a position in which it fits closely around the catheter in the vicinity of its distal end.

Prosthesis 15 is surrounded by a crocheted material 14 formed by a continuous thread, with successive meshes wrapped around the prosthesis alternately on one side or the other, in other words alternately on the right or left side. The initial section 17 of the thread material, located in front of the first mesh 16 associated with the distal end 12 of catheter 11, is pulled through a slot 18 in the catheter wall, pinched in said slot, and then extends through the catheter lumen and out through the distal end of the catheter. A strippable loop 22 is pulled through a knot 21 that closes end mesh 20 which is remote from the distal end, said loop being pulled through two cuts 23, 23' in the catheter wall, and is therefore likewise held axially by pinching.

The free thread end guided through knots 21 of said end mesh 20 forms a drawstring 24 extending along catheter 11, by means of which drawstring, first loop 22 held on the catheter by pinching and then gradually the mesh formed of crocheted material extending around the prosthesis and holding the latter in its compressed state, can be stripped through said end knot. Since the meshes are wrapped alternately right and left around prosthesis 15, when the mesh is stripped the threads on the right and left sides of the catheter are released alternately from the corresponding mesh knots, and after the mesh facing the distal end comes loose, initial segment 17 of the thread material can be pulled out of its pinched position in slot 18 at distal end 12 of catheter 11.

Figure 2:
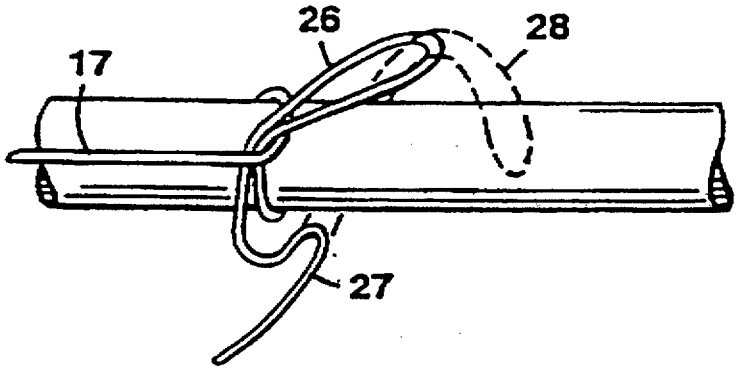
FIG. 2 is a view showing the formation of an initial mesh of crocheted material on the prosthesis, with a loop brought around the vascular prosthesis on the right side.
Figure 3:
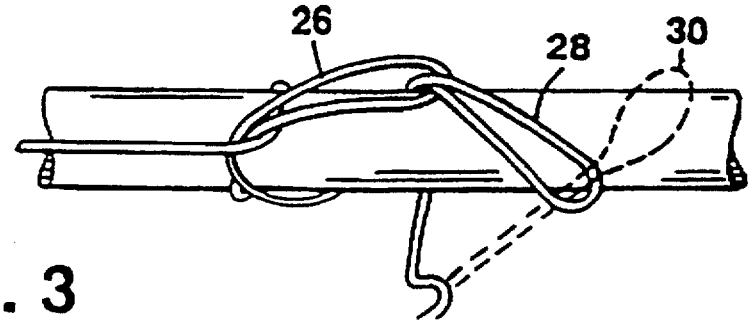
FIG. 3 is a view like that in FIG. 2, showing the formation of a crocheted mesh adjoining the initial mesh, wrapped around the vascular prosthesis on the left side.

In an enlarged view, FIGS. 2 and 3 show the mesh formation with alternate front and back wrapping of catheter 15, which in these figures is shown as a rigid tubular structure for the sake of simplicity. After securing initial section 17 of the thread material in the manner shown in FIG. 1 by pinching in slot 18, the thread is wrapped around the catheter, then a loop 26 is pulled through under the thread, and then from free thread material 27, a mesh on the back of the catheter is pulled around the latter and passed through loop 26, whose section pulled through the above loop 26 in turn forms a loop 28 to form the next mesh. FIG. 2 shows free thread material 27 in solid lines before it is pulled through loop 26, and shows it in dashed lines after it is pulled through this loop and forms loop 28 for the next mesh.

To form the next mesh, as shown in FIG. 3, forming another loop 30 in the manner shown by the dashed lines, the free thread material is pulled out of the position shown at 31 in front of the catheter, through previously formed loop 28, and then this process of loop and mesh formation is continued, with the thread material pulled alternately behind and in front of the catheter through the respective loops until the prosthesis held in the catheter is crocheted over its entire length.

Loop 22, pulled through the loop associated therewith or through a knot 21 formed by pulling together these loops to form end mesh 20, is then pulled in the manner shown schematically in FIG. 1 through the two axially spaced slots 23, 23' in the wall of the catheter and held in place by pinching. The remaining thread material then forms drawstring 24 which extends from the loop of end mesh 20 and permits the crocheted material to be stripped, with the thread material of the meshes as they are stripped alternately coming loose on one side or the other of prosthesis 15, thereby releasing the prosthesis to expand under the pretensioning force imposed during crocheting as a result of radial compression.

Figure 4:
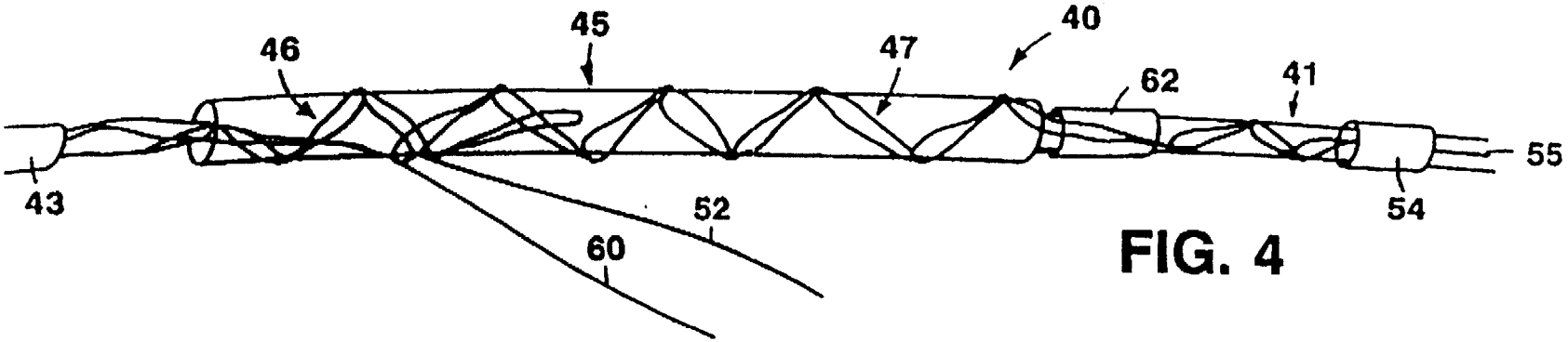
FIG. 4 is a view similar to FIG. 1, showing a design for a device in which the vascular prosthesis mounted on the catheter is held in its compressed state with radial pretensioning by means of strippable crocheted material mounted on the distal and proximate ends.

In embodiment 40 shown in FIG. 4, a prosthesis 45 is mounted and held in its compressed position under radial pretensioning on an elongated catheter 41 in the vicinity of distal catheter end 42. This purpose is served by crocheted material 46, 47 shown in FIGS. 5 and 6. Catheter 41, like catheter 11 of the embodiment shown in FIG. 1, is advanceable by means of a guide wire located in a vessel, in said vessel so that prosthesis 45 mounted on the catheter is implantable positionwise in the vessel prior to its implantation by stripping the crocheted material.

The crocheted material that holds prosthesis 45 in the compressed position shown in FIG. 4 is applied sequentially, with crocheted material 46 starting at the distal end. The other crocheted material 47 is applied from the proximal end and then overlaps the end of the first crocheted material 46.

Figure 5:
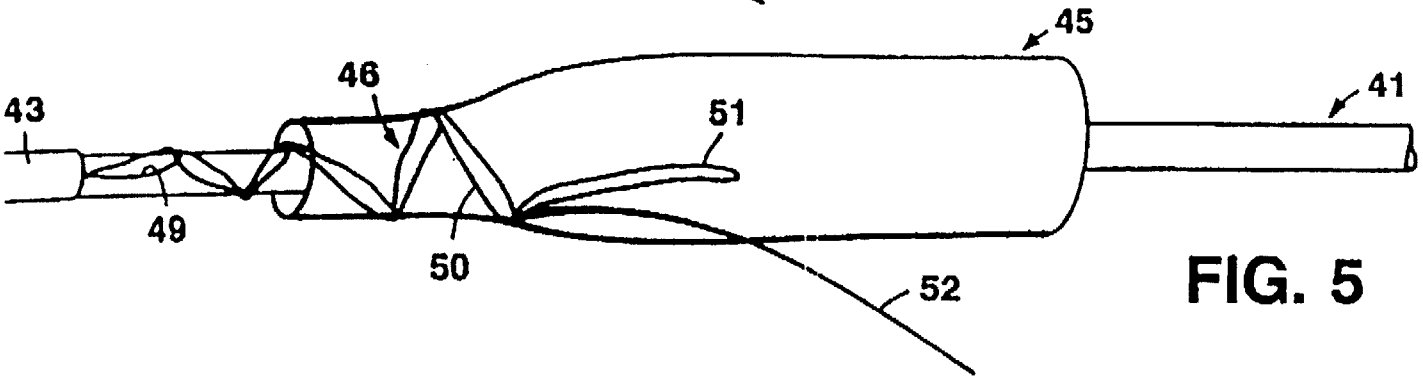
FIG. 5 shows the device according to FIG. 4 but with the crocheted material applied from the distal end.

FIG. 5 shows that catheter 41 is provided on the distal end with a silicone cuff 43, which serves to hold the initial segment 48 of the thread required for the formation of the first crocheted material. For this reason, initial segment 48 of this thread is pulled through beneath silicone cuff 43. Then the first meshes 49, in the manner explained above in conjunction with FIGS. 1 to 3, are crocheted on catheter 41, and provide a firm seat on the catheter for the first crocheted material. Subsequent meshes 50 fit over the end of prosthesis 41 that points toward the distal end of the catheter, and compress the latter under radial pretensioning with simultaneous axial immobilization of the prosthesis on the catheter, as shown in FIG. 5. A final mesh 51 of this crocheted material 46 is then applied externally on prosthesis 45, with thread 52 extending from this mesh as a drawstring to strip the mesh of the above-mentioned crocheted material.

Figure 6:
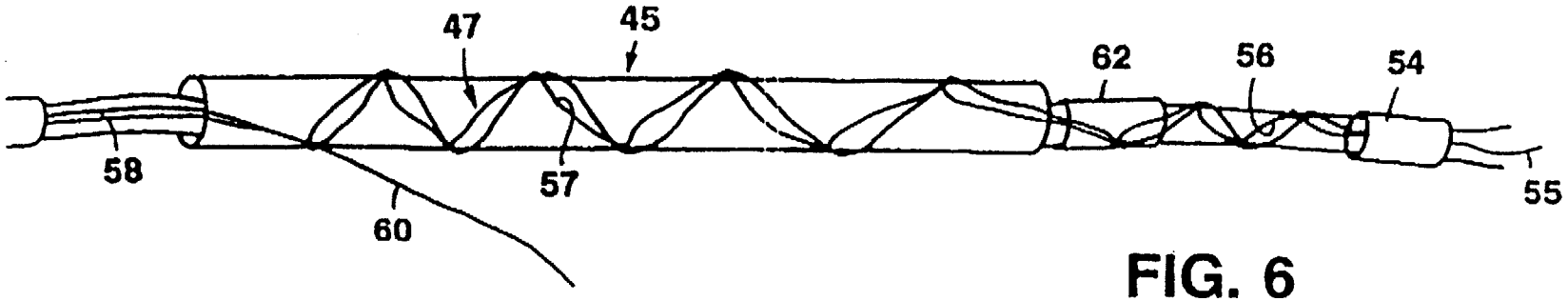
FIG. 6 shows the device according to FIG. 4 with the crocheted material applied from the proximal end alone, eliminating the crocheted material shown in FIG. 5.

FIG. 6 shows the application of the second crocheted material 47 from the proximal end. Beginning 55 of the thread material of this crocheted material is again held by means of a silicone cuff 54 pulled onto the proximal end of catheter 41, while the beginning of the thread is pulled through beneath this cuff. Then several meshes 56 are crocheted onto the catheter in the direction of the distal end, followed by additional meshes 57, while wrapping prosthesis 41 during its simultaneous radial compression up to and beyond meshes 50, 51 of the first crocheted material 46 facing away from the distal end, which are held thereby. A last mesh 58 of the crocheted material 47 applied from the proximal end is then pulled through under silicone cuff 43 pushed onto the distal end of the catheter, and held thereby. In addition, thread 60 extends from the end mesh facing the distal end of the crocheted material 47 applied from the proximal end, as a drawstring to strip the mesh of this crocheted material.

The prosthesis 45 in the embodiment shown in FIGS. 4 to 6, like that in the embodiment shown in FIGS. 1 to 3, is held under radial pretensioning in the compressed position on catheter 41 and automatically expands to its expanded position after removal of crocheted material 46, 47. Following introduction of the prosthesis mounted on the catheter into a vessel and its location in place, implantation occurs in such fashion that crocheted material 46 applied from the distal end is removed first. This is accomplished by stripping the mesh of this crocheted material by means of drawstring 52, with mesh 51 located beneath the crocheted material applied from the proximal side being stripped first and then gradually meshes 50 and 49 abutting the distal end being stripped until eventually the first mesh adjacent to silicone cuff 43 comes free and the beginning of thread 48 beneath the silicone cuff is pulled out.

Since the end of the prosthesis that points toward the distal catheter end is released by stripping crocheted material 46 applied from the distal end, this end of the prosthesis expands radially as a result of the pretensioning forces of the prosthesis itself, while the remaining part of the prosthesis is still held in the compressed position by crocheted material 47 applied from the proximal end. Partially expanded prosthesis 45 is axially immobilized in this position both by the adhesive effect between the catheter and the prosthesis and by a silicone cuff 62 mounted on the proximal end of prosthesis 45 on catheter 41, which cuff the prosthesis abuts axially.

After stripping first crocheted material 46, crocheted material 47 applied from the proximal end is also stripped, specifically by means of drawstring 60 extending from its end mesh 58 on the side pointing toward the distal end. It is clear that when the drawstring is pulled, loop 58 held at the distal end beneath silicone cuff 43 is stripped first and then meshes 57 and 56 are stripped, starting at the side facing the distal end, gradually in the direction of the proximal end, with prosthesis 45 expanding radially and abutting the walls of a vessel to be equipped with a prosthesis. At the end of the stripping process, thread end 55 located beneath silicone cuff 54 at the proximal end is pulled free. Prosthesis 45 is then free of catheter 41 and the latter can be withdrawn in simple fashion out of the vessel.

Prosthesis 70 shown in FIG. 7 is likewise tubular in shape and self-expanding. It can be a meshwork, roughly in the form of a knitted fabric. The prosthesis is provided with holes 71, 72 associated with one another pairwise and located at approximately equal axial distances from one another. Loops 74 surrounding the prosthesis externally hold the prosthesis together in its radially compressed state. These loops are thread material, each pulled through a hole 71, of a thread 75 running along the inside of the prosthesis, said thread then surrounding the prosthesis forming a loop with tension, and with loop end 76, each being introduced through a hole 72 corresponding to matching hole 71, back into the interior of the prosthesis. The loops are held in the wrapping position shown in FIG. 7 by means of a warp thread 78 guided through loop ends 76 inside the prosthesis.

The advantage of the embodiment shown in FIG. 7 consists in the fact that loops 74 wrapped around the prosthesis at essentially constant axial intervals are used as means for radial compression of prosthesis 70, said loops having no external knots at all but formed by a thread 75 running along the inside of the prosthesis and held in the tensioned position by means of the warp thread 78 likewise running along the inside of the prosthesis.

The prosthesis according to FIG. 7, in the same way as described above in conjunction with FIGS. 1 to 6, is mounted in a radially compressed state on a catheter in the vicinity of the distal catheter end, and is implantable by means of the catheter by advancing the latter in a vessel. Following correct positioning in the vessel, implantation is accomplished in simple fashion by pulling warp thread 78 out of ends 76 of loops 74, whereupon prosthesis 70 expands radially under its own spring pretensioning force to its proper expanded position. Thread 75 which is pulled to form the loop can then likewise be simply pulled back.

The embodiment shown in FIG. 8 differs from the embodiment in FIG. 7 in that loops 74 surrounding prosthesis 70' and spaced axially apart are formed by crocheting. Through a hole 71' in the prosthesis, thread material from thread 75 guided along the interior of the prosthesis is pulled out and wrapped as a loop 74' around the prosthesis, and is also introduced through a hole 72' spaced axially from above-mentioned hole 71', together with loop end 76', back into the interior of the prosthesis. Thread material is then pulled through this loop end 76' located in the interior of the prosthesis, forming another loop and guided externally through a hole 71' following in the axial direction, then is wrapped again around the prosthesis as loop 74' and secures the loop end, brought back into the interior of the prosthesis through another hole 72', in the same manner as the first loop.

Referring to FIG. 9, a knitted intravascular prosthesis 80 (partial view to illustrate component threads) is shown in which a thread 81 of resorbable material and a thread 82 of non-resorbable material are knitted together alternately. The non-resorbable thread material can be tantalum for example.

The advantage of this prosthesis design consists in the fact that the resorbable thread material dissolves following expiration of a predetermined period of time after implantation, and then only the non-degradable components remain in the body of a patient. These remaining components form circular rings of successive open loops. In this manner, thread crossings are avoided, which could exert unnecessary shearing forces on the surrounding and growing tissue coatings.

Prostheses according to FIG. 9 can also be designed in simple fashion as drug deposits with drugs being imbedded in the resorbable thread material and released as this material degrades.

1 claim:

1. In combination, a device with a prosthesis implantable in a body of a patient, said prosthesis designed as a hollow body and being compressible against restoring spring forces to a cross section which is reduced relative to an expanded use position, said prosthesis also, after removal of restraining forces that maintain said prosthesis in reduced cross section, expanding automatically to a cross section that corresponds to the use position, wherein said device is a strippable sheath formed of at least one continuous thread surrounding said prosthesis in said reduced cross section, and at least one drawstring being layable to extend from the sheath that holds the prosthesis in reduced cross section, said drawstring being retractable to effect automatic expansion of said prosthesis by removing said sheath.

2. The device according to claim 1 wherein the sheath holding the prosthesis in reduced cross section is a strippable meshwork.

3. The device according to claim 1 wherein the prosthesis, held in reduced cross section by the strippable sheath, is mounted on a probe advanceable into a body lumen.

4. The device according to claim 3 wherein said probe is an elongate catheter with a distal insertion end for entry into a body lumen and a proximal end, said prosthesis, held in reduced cross section by the strippable sheath, being held in an axially fixed manner on the insertion end of said probe.

5. The device according to claim 4 wherein the probe for advancing the prosthesis includes a lumen so the probe can be advanced over a guide wire.

6. The device according to claim 3 wherein the prosthesis is mounted on a nonslip substrate which is mounted on the probe.

7. The device according to claim 3 wherein a first end of the thread forming the sheath and a second end of the thread forming an end loop of the sheath are secured *at* positions on the probe and releasable by pulling the drawstring.

8. The device according to claim 7 wherein the first and second ends of the thread forming the sheath are pinched in holes of the probe.

9. The device according to claim 7 wherein the first end of the thread forming the sheath is pinched between the probe and an elastic cuff.

10. The device according to claim 7 [including a sheath with an] *wherein the* end loop *is* attached to the probe and [one] *the second* end of the thread [forming said end loop extending] *extends* from a slipknot to form said drawstring.

11. The device according to claim 3 wherein the [prosthesis is held in its radially compressed position by means of a] sheath [of] *includes* a first strippable meshwork applied from the distal end of the probe and a second strippable meshwork applied in the opposite [axial] direction [thereto,] from the proximal end[,] *of the probe* and extending over an end loop of the first meshwork.

12. The device according to claim 11 wherein said meshworks are strippable in opposite axial directions by drawstrings.

13. The device according to claim 3 wherein at least one end of the prosthesis is surrounded in the compressed state by a cuff on the probe, said prosthesis escaping from the cuff as a result of axial shortening that takes place during the expansion of the prosthesis.

14. The device according to claim 3 wherein an end of the prosthesis facing away from [the] *an* insertion end *of the probe* abuts a radial projection on the probe.

15. The device according to claim 3 wherein the drawstring is fed through a lumen in the probe and through a hole in the probe lumen that passes through a probe wall in the vicinity of one end of the prosthesis, said lumen extending to the proximal end of the probe.

16. The device according to claim 15 wherein the probe is a double-lumen catheter, with one lumen being used to advance the catheter over a guide wire and the drawstring for the meshwork surrounding the prosthesis being passed through the other lumen.

17. The device according to claim [1] *52* wherein the prosthesis is a mesh tube including metal thread material.

18. The device according to claim 17 wherein the prosthesis has successive mesh rows alternately made of resorbable and nonresorbable thread material.

19. The device according to claim 18 wherein drugs are embedded in *the* resorbable thread material for enabling drug deposit by said prosthesis.

20. The device according to claim 18 or 19 wherein said non-resorbable material is a metal.

21. The device according to claim 19 wherein the sheath has successive mesh loops formed in opposite circumferential directions around the prosthesis, so that when successive mesh loops are stripped, the thread segments forming the loops come loose alternately on the right and left from the prosthesis.

22. The device according to any one of claims [1] *52*, 2, 3, 5, or 17 wherein the sheath has successive mesh loops formed in opposite circumferential directions around the prosthesis, so that when successive mesh loops are stripped, the thread segments forming the loops come loose alternately on the right and left from the prosthesis.

23. The device according to claim 22 wherein the sheath surrounding the [strippable tube] *prosthesis* is formed of a patterned thread material.

24. The device according to claim 22 wherein the sheath surrounding *the* prosthesis is *a* strippable tube manufactured by crocheting.

25. The device according to claim 24 wherein knots of said strippable loops of the surrounding sheath are arranged so that adjacent knots lie respectively on opposite sides of the sheath.

26. The device according to claim 24 [or 25] wherein knots of said strippable loops of the surrounding sheath are arranged such that alternate knots lie axially sequentially in rows.

27. The device according to any one of claims [1] *52*, 2, 3, 5, or 17 wherein the drawstring extends from a portion of the sheath surrounding a distal insertion end of the prosthesis so that when the sheath is stripped, the prosthesis gradually expands from the distal end to the proximal end.

28. The device according to claim [1] *52* wherein an end of the thread forming the sheath is held by a strippable slipknot.

29. The device according to any one of claims [1] *52*, 3, or 17 wherein the sheath holding the prosthesis in its radially compressed position is formed of successive wrapping loops wrapped around the prosthesis at axial distances from one another, said wrapping loops being of a thread material extending along the inside of the prosthesis and pulled through a first hole in the prosthesis, the ends of said wrapping loops being guided back through a second hole in said prosthesis circumferentially adjacent to the first hole, and into the interior of the prosthesis, and said device further including a warp thread, running along the inside of the prosthesis and guided through the ends of the loops, the warp thread holding the loops in their wrapped positions.

30. The device according to any one of claims [1] *52*, 3, or 17 wherein the sheath holding the prosthesis in its radially compressed position is formed of wrapping loops wrapped around the prosthesis at axial distances from one another, said wrapping loops being of a thread material extending along the inside of the prosthesis and pulled through a first hole in the prosthesis, ends of said loops guided back into the interior of the prosthesis through a second hole spaced axially from the first hole, the wrapping loops being held in wrapping position by a loop formed from the thread material running inside the prosthesis being pulled through the end of the wrapping loop positioned inside the prosthesis, said loop passing through the end of the wrapping loop then extending outward through an adjacent hole in the axial direction and being wrapped around the prosthesis to form an adjacent wrapping loop.

31. The device according to claim [1] *52* or 17 wherein the sheath is formed of shrinkable thread material.

32. The device according to claim [1] *52* or 17 wherein the strippable sheath [is] *includes* a plurality of threads running parallel to one another.

33. The device according to claim [1] *52* or 17 wherein at least two sheaths are provided wherein a first one of the two sheaths holds the prosthesis in the radially compressed state and a second sheath fits loosely around the prosthesis such that when the first sheath is stripped, the second sheath permits partial expansion of the prosthesis, said second sheath being subsequently strippable itself to permit full expansion.

34. The device according to claim [1] *52* wherein the sheath is a meshwork surrounding the prosthesis with spaces between meshes filled and smoothed with a substance that dissolves in the body of a patient.

35. The device according to claim [1] *52* wherein the thread [material] forming the sheath is provided with a lubricant to reduce friction.

36. The device according to claim [1] *52* wherein at least the drawstring is constructed with metal so that it is visible in an x-ray image.

37. The device according to claim [1] *52* wherein the proximal end of the prosthesis is flared in the expanded state, following removal of the sheath.

38. The device according to claim [1] *52* or 17 wherein said prosthesis is formed by a patterned thread material.

39. The device according to claim [1] *52* or 17 wherein said prosthesis is a knitted mesh tube.

40. The device according to claim [1] *52* or 17 wherein said prosthesis is a crocheted mesh tube.

41. The device according to claim [1] *52* wherein said prosthesis is a mesh tube composed of plastic thread material.

42. The device of claim [1] *52* or 35 wherein the thread forming said sheath is provided with a lubricant.

43. A system for implanting a prosthesis at a desired location in a body lumen, comprising:

a catheter constructed for percutaneous delivery, including a distal portion for receiving and carrying said prosthesis to said location, and a prosthesis release control mesh formed of a thread-like strand and surrounding said prosthesis for substantially its entire length, said release-control mesh being capable of maintaining said prosthesis on said catheter and said release control mesh further capable of being controllably unraveled from one end to the other by pulling an end of said thread-like strand to release said prosthesis from said catheter and allow it to be expanded into engagement with said body lumen at said desired site.

44. The system of claim 43 wherein said release-control mesh is a mesh of the type formed by forming a first loop [over said wrapped portion] that extends over one end of said prosthesis, a free end of said thread being formed into a second loop which is wrapped around said prosthesis and through said first loop, and the process *being* repeated to form additional loops which are wrapped about said prosthesis until the entire length of said prosthesis has been wrapped and said mesh terminates in an end loop.

45. The system of claim 43 wherein a free end of said thread [from said] *forms an* end loop *and* extends to the proximal end of said catheter, whereby pulling said thread [will release] *removes* said end loop from said [catheter] *free end of thread* and continued pulling [will unravel] *unravels* said mesh from one end to the other releasing said prosthesis from one end to another.

46. The system of claim 45 wherein the end loop of said mesh is releasably secured to said catheter.

47. The system of claim 46 wherein said end loop is releasably secured by an elastic sleeve attached to said catheter.

48. The system of claim [47] *44* wherein the first loop is releasably secured to said catheter by an elastic sleeve attached to said catheter.

49. The system of claim 45 wherein said free end of said thread extends through a lumen in said catheter to said proximal end.

50. The system of any one of claims 43–49 wherein said mesh unravels from the distal end to the proximal end.

51. The system of any one of claims 43–49 wherein said prosthesis is a self-expanding prosthesis of the type that expands under spring force.

*52. In combination, a device with a prosthesis implantable in a body of a patient, said prosthesis designed as a hollow body and being compressible against restoring spring forces to a cross section which is reduced relative to an expanded use position, said prosthesis also, after removal of restraining forces that maintain said prosthesis in reduced cross section, expanding automatically to a cross section that corresponds to the use position, wherein said device comprises at least one strippable sheath formed of at least one continuous thread surrounding said prosthesis in said reduced cross section, and at least one drawstring extending from the sheath that holds the prosthesis in reduced cross section, said drawstring being retractable to effect automatic expansion of said prosthesis by removing said sheath.*

* * * * *